United States Patent [19]
Townley

[11] Patent Number: 6,096,084
[45] Date of Patent: Aug. 1, 2000

[54] MODULAR BALL AND SOCKET JOINT PREFERABLY WITH A CERAMIC HEAD BALL

[75] Inventor: Charles O. Townley, Port Huron, Mich.

[73] Assignee: BioPro, Inc., Port Huron, Mich.

[21] Appl. No.: 09/148,842

[22] Filed: Sep. 4, 1998

[51] Int. Cl.[7] ........................................................ A61F 2/36
[52] U.S. Cl. ..................... 623/23.12; 623/23.14
[58] Field of Search ................................. 623/16, 18, 19, 623/22, 23

[56] References Cited

U.S. PATENT DOCUMENTS

| | | | |
|---|---|---|---|
| 2,934,065 | 4/1960 | Townley ..................................... | 623/23 |
| 4,012,795 | 3/1977 | Doore et al. ............................... | 623/23 |
| 4,752,296 | 6/1988 | Buechel et al. ............................ | 623/23 |
| 5,549,704 | 8/1996 | Sutter ........................................ | 623/23 |

OTHER PUBLICATIONS

BioPro, Inc, "PSL Total Hip Replacement System," brochure, 1991, with re–publication thereof 1997.
Townley, *Orthopedic Clinics of North America*, vol. 13, No. 4, Oct. 1982, "Hemi and Total Articular Replacement Arthroplasty of the Hip with the Fixed Femoral Cup."
BioPro, Inc., "The Biopro Tara Surgical Procedure," brochure, Feb. 1998.
ASTM F 1537–94, 1994.
ASTM F 799–95, 1995.
BioPro, Inc., "The Biopro Ceramic Tara," brochure, Oct. 1997.
BioPro, Inc., "Total Articular Arthroplasty for the Hip Joint, T.A.R.A., Utilizing Ceramic–on–Polyethylene," brochure, Mar. 1998.
Hulbert, *Transactions of the 24th Annual Meeting of the Society for Biomaterials*, Apr. 22–26, 1998, San Diego, California, p. XLV: "The Use of Ceramics in Surgical Implants—How I Met C. William Hall."

(List continued on next page.)

*Primary Examiner*—David J. Isabella
*Attorney, Agent, or Firm*—Christopher John Rudy

[57] ABSTRACT

Modular ball and socket joint has 1) a cupped ball head, preferably of ceramic, having a support body with an inferior, deep, distally facing, preferably generally planar, surface having a substantially circular outer boundary thereto; a distally opening stem receiving bore preferably centrally located in the support body; a cup wall, extending distally from the support body and having a preferably substantially cylindrical inner surface which extends from said outer boundary of said distally facing surface; and a superficially facing, generally semispherical, smooth external surface, preferably and optimally of a low friction coefficient, encapsulating the support body and cup wall; and 2) an interchangable and modular stem, preferably of metal or metal alloy, having a distally directed spike, and a superior stem cap which is insertable into the bore of the head; optionally with 3) a head-receiving articular cup having an inner articular surface and a mountable back surface, the articular surface of which, when the head-receiving cup is suitably mounted in suitable receiving stock, mates in articulating contact with said smooth external surface of said head when said head and stem are suitably mounted in suitable receiving stock. The head and stem modularity allows for noticeably increased versatility and efficiency in surgical procedures, and the ceramic material is beneficially adapted for employment in the fabrication of femoral resurfacing implants for conservative arthroplasty.

18 Claims, 3 Drawing Sheets

OTHER PUBLICATIONS

Jacobs, *Transactions of the 24th Annual Meeting of the Society for Biomaterials*, Apr. 22–26, 1998, San Diego, California, p. XLVII: "Wear—the Clinical Problem: Total Hip Replacement."

Benezra et al., *Transactions of the 24th Annual Meeting of the Society for Biomaterials*, Apr. 22–26, 1998, San Diego, California, p. 63: "Ultrastructure and Adhesion of the Scale on Oxidized Zr–2.5Nb for Total Joint Arthroplasty."

Hampel et al., *Transactions of the 24th Annual Meeting of the Society for Biomaterials*, Apr. 22–26, 1998, San Diego, California, p. 96: "Relationship Between Femoral Head Sliding Path and Three–Dimensional Wear Volumes in Total Hip Replacement."

Townley, *Ceramic Transactions*, vol. 48, pp. 23–34 (1995), "Complications in Total Hip Replacement: Etiology, Prevention and the Role of a Ceramic Articulation."

Kue et al., *Transactions of the 24th Annual Meeting of the Society for Biomaterials*, Apr. 22–26, 1998, San Diego, California, p. 118: "Enhanced Proliferation and Osteocalcin Production by Human Osteoblast–Like Cells on Silicon Nitride Ceramic Discs."

Bellare et al., *Transactions of the 24th Annual Meeting of the Society for Biomaterials*, Apr. 22–26, 1998, San Diego, California, p. 124: "Quantitative Evaluation of Degree of Consolidation in UHMWPE Components."

Villermaux et al., *Transactions of the 24th Annual Meeting of the Society for Biomaterials*, Apr. 22–26, 1998, San Diego, California, p. 215: "Zirconia–Alumina Pairing for Hip Prosthesis Applications: Comparision to Common Head–Cup Systems on a Hip Joint Simulator with Different Lubricants."

Blaise et al., *Transactions of the 24th Annual Meeting of the Society for Biomaterials*, Apr. 22–26, 1998, San Diego, California, p. 249: "Stress Analysis of Ceramic–Ceramic Pairing for Hip Prosthesis Applications."

Clineff et al., *Transactions of the 24th Annual Meeting of the Society for Biomaterials*, Apr. 22–26, 1998, San Diego, California, p. 445: "Characteristics of UHMWPE Wear Debris Associated with Failed Femoral and Stable Acetabular Components of Total Hip Replacements (THR)."

Amstutz et al., *Transactions of the 24th Annual Meeting of the Society for Biomaterials*, Apr. 22–26, 1998, San Diego, California, p. 447: "The Critical Difference in Hemi–surface Replacement vs. Total Hip Resurfacing: Absence of a Polyethylene Acetabular Component."

Food and Drug Administration (FDA) letter to BIOPRO giving Section 510(k) approval, with enclosure, Jan. 6, 1997.

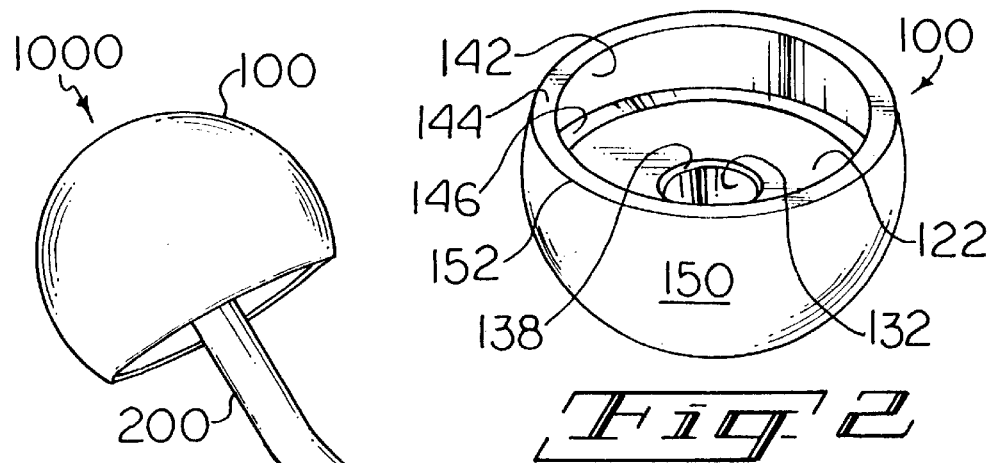
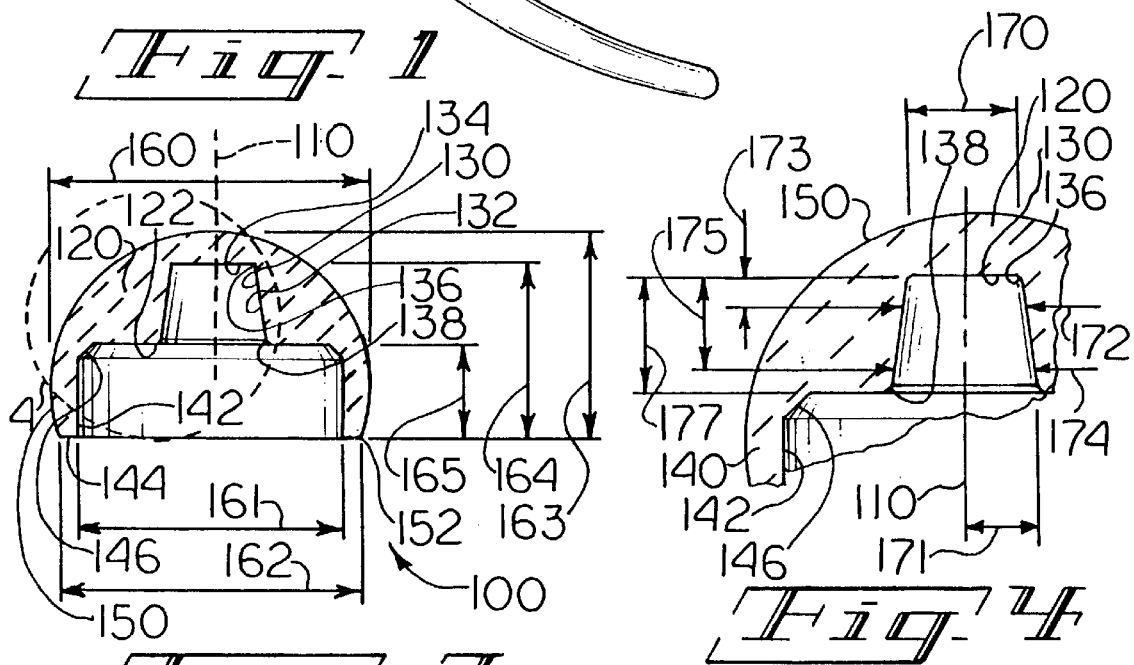
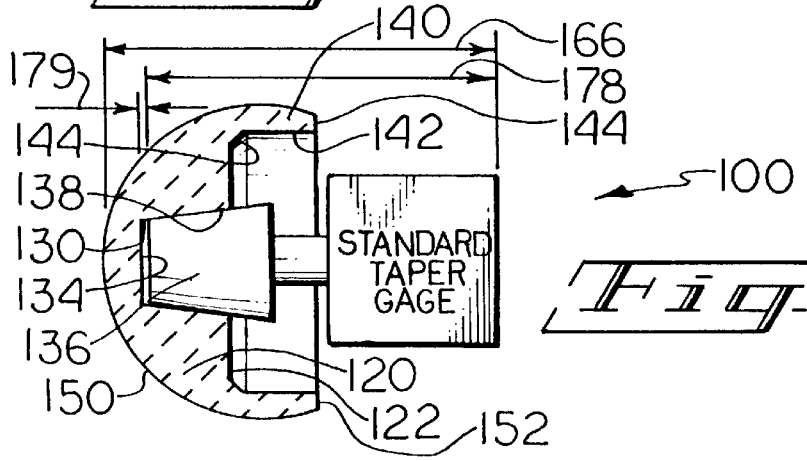

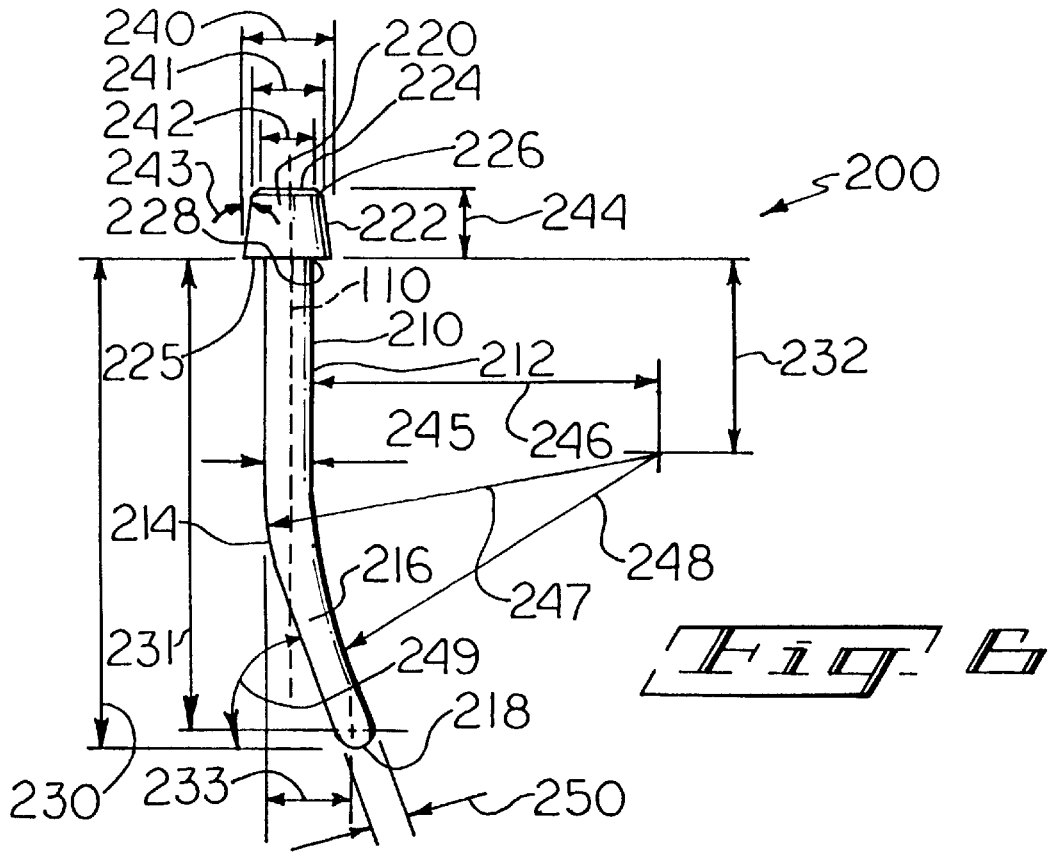
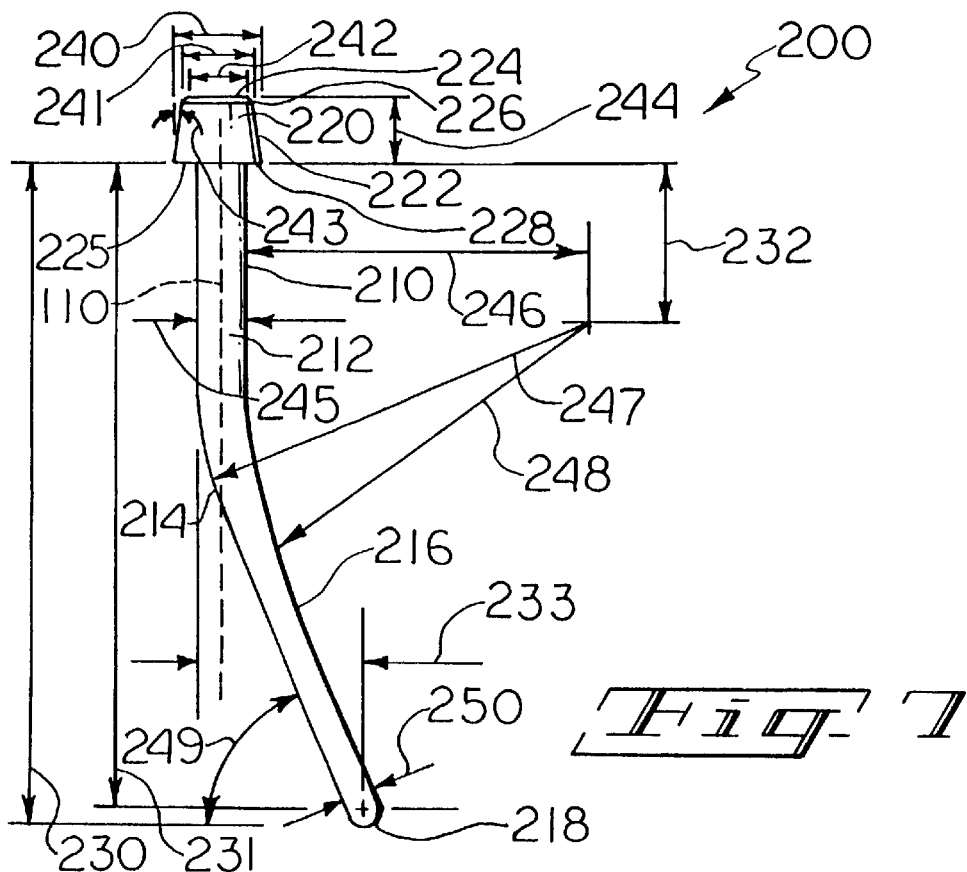

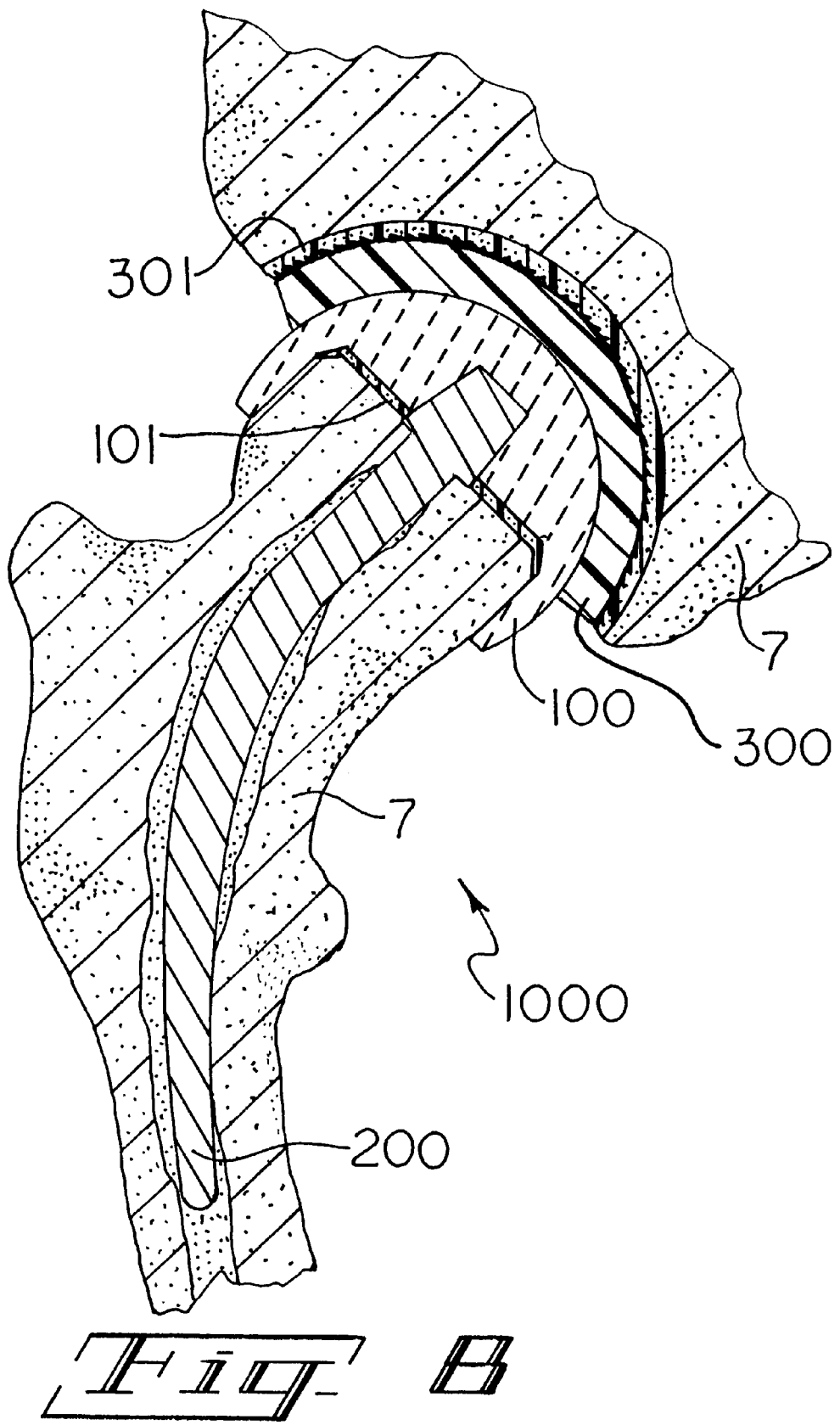
Fig. B

MODULAR BALL AND SOCKET JOINT PREFERABLY WITH A CERAMIC HEAD BALL

FIELD AND PURVIEW OF THE INVENTION

The present invention concerns a modular, multi-part, stem and head, enarthrodial type joint ensemble, useful in general in arthroplasty and in particular in articular surface replacement arthroplasty. In a preferred embodiment, the joint of concern is the hip. As such, it is believed that the ensemble is the first known hip implant system for replacement of the femoral head, in bone-preserving, conservative resurfacing hip arthroplasty which employs a ceramic head—as well the first known resurfacing hip implant system which employs modular stem and head components.

BACKGROUND TO THE INVENTION

By way of introduction, in the hip implant field, two main arts may be delineated: on one hand is conventional hip replacement arthroplasty, where all of the femoral neck and head is replaced with a prosthetic implant; on the other hand is articular resurfacing, also known as conservative hip replacement, in which event only the outer articulating portion of the femoral head is replaced with a much thinner, bone-preserving implant. In each instance, the procedure may be limited to a hemiarthroplasty by replacing only the femoral side of the hip, leaving the implanted femoral component to articulate with the acetabulum's own socket; or it may be extended to a total joint arthroplasty by also replacing the socket side of the joint with a matching acetabular component implant.

Femoral components with ceramic heads are known for conventional hip replacement.

And, interchangeable, modular implants are not routinely employed for conventional hip replacement.

conventional hip replacement itself may be associated with several drawbacks, among these, the great amounts of bone which must be resected so as to accommodate the femoral component. See, e.g., the brochure from BioPro, Inc., "PSL Total Hip Replacement System." In addition, a less than desirably natural postoperative gait may result.

With respect to the pertinent, conservative resurfacing art, Townley, Charles O., M.D., *Orthopedic Clinics of North America*, Vol. 13, No. 4, October 1982, "Hemi and Total Articular Replacement Arthroplasty of the Hip with the Fixed Femoral Cup," reported on detailed information concerning the design rationale and surgical technique for the total articular replacement arthroplasty (TARA) conservative hip procedure. Subsequent thereto, the component design and implantation technique have remained essentially unchanged except for the development of improved instrumentation to remodel the femoral head, and the conversion to porecoated, uncemented implants in conjunction with a self-locking, metal-backed acetabular component in 1985. See also, the brochure from BioPro, Inc., "The Biopro Tara Surgical Procedure."

Prior femoral head hip resurfacing components have been machined from metallic materials, to include cobalt-chrome, stainless steel, and titanium.

And, with respect to the resurfacing art, femoral components have been designed as one-piece, inseparable stem and cup items.

Some drawbacks in the foregoing articular resurfacing systems include, first, a less than desirable smoothness (micro finish) of the articulating surface of the metallic prosthesis, which is typically a four to five millionths of an inch micro finish; and second, the presence of a one-part femoral component.

The first drawback mentioned above with respect to the articular resurfacing art is reflected in the incidence of latent, friction-induced postoperative complications which adversely impact survivorship longevity of the arthroplasty as a consequence of the limitation in the obtainable surface smoothness of the metallic femoral resurfacing component in current use. In the experience of the inventor, the predominant, singular complication in the case of a metal-on-polyethylene Total Articular Replacement Arthroplasty relates to a sequential, friction-induced scenario of polyethylene wear degradation; the consequent proliferation and dissemination of wear debris which accesses the supporting bone-prosthesis interface, which, in turn, precipitates a debris-induced foreign body reaction and an associated degree of periprosthetic osteolysis, sufficiently severe to culminate in an implant failure rate on the order of fifteen percent with an average post-operative failure time of some ten years. In case of femoral hemiarthroplasty, the procedure is not infrequently followed by variable degrees of friction-induced pain and latent acetabular wear protrusio associated with the unreplaced socket articulation, which, in either event, may require additional surgical intervention.

The second drawback mentioned above with respect to the articular resurfacing art is reflected in the adverse economic impact associated with the pre-fixed, inseparable, non-modular arrangement of the two-part prosthesis. The same requires a redundant, costly on-shelf inventory of implants to accommodate the individual anatomic variance between the size of the femoral head and the configuration of the medullary canal of the proximal femur in patients consigned for resurfacing arthroplasty. Economic considerations aside, the concept of a one-piece, non-modular system with its fixed combinations of femoral head and stem sizes may not fit the anatomical needs of a given patient relative to one or the other of its stem and head (cup).

SOME DESIDERATA WITH RESPECT TO THE INVENTION

In general, it would be desirable to provide improved ball and socket type replacement joints, particularly for the hip. In view of the aforementioned drawbacks, it would be desirable to provide, in particular, a hip joint implant which can engender more conservative surgical practice, is adaptable to various bodily differences, has high survivorship, is more efficiently provided overall, and can be used in either hemiarthroplasty resurfacing or in total articular replacement arthroplasty.

SOME OBJECTS OF THE INVENTION

It is an object of the present invention to provide a joint system which can increase surgical versatility and proficiency in bone-conserving hip resurfacing procedures.

It is another object of the invention to improve postoperative results following upon hip resurfacing.

It is still another object of the invention to satisfy one or more of the foregoing objects with respect to other enarthrodial joint systems.

Further objects hereof are extant.

SUMMARY OF THE INVENTION

The present invention provides a modular, bone-preserving, conservative, resurfacing arthroplasty, ball and socket joint implant, which comprises the following components:

a cupped ball head having a support body with an inferior, deep, distally facing surface having an outer boundary thereto; a distally opening stem receiving bore located in the support body;

a cup wall, extending distally from the support body and having an inner surface which extends from said outer boundary of said distally facing surface; and a superficially facing, generally semispherical, smooth external surface encapsulating said support body and cup wall; and a stem having a distally directed spike, and a superior stem cap which is insertable into the bore of said head;

optionally with a head-receiving articular cup having an articular surface and a mountable back surface, the articular surface of which, when the head-receiving cup is suitable mounted in suitable receiving stock, mates in articulating, gliding contact with said smooth external surface of said head when said head and stem are suitably mounted in suitable receiving stock.

The invention is designed for use and finds its utility in conservative joint resurfacing arthroplasty.

Significantly, by the present invention, problems in the art are ameliorated if not overcome, with one, more or all of the aforementioned desiderata and objects being satisfied. Among its advantages, the present invention allows for noticeably increased versatility and efficiency in surgical procedures, as the proper components can be mixed and matched with the physical needs of the patients in mind. The invention, as well, with the surgeon able to so mix and match components, provides for a more economical system with respect to manufacture and materials utilization. Of great significance, ceramic material is now beneficially adapted for employment in the fabrication of femoral resurfacing implants for conservative arthroplasty. In relation to metal, the ceramic can have a much lower coefficient of friction with particular respect to an articulating surface, and as a consequence, both total and hemiarticular arthroplasties may be made to be more successful. As well, the sizes of the femoral heads, for example, are modeled upon naturally sized heads, and furthermore, less bone stock is resected with the joint of the invention that that which is resected in conventional hip replacement. Not only hips but also other enarthrodial joints may be surgically revised herewith.

Numerous further advantages attend the invention.

BRIEF DESCRIPTION OF THE DRAWINGS

The drawings form part of the specification hereof. With respect to the drawings, the following is briefly noted:

FIG. 1 is a bottom, perspective view of a modular ceramic ball and socket joint of the invention, with its head and stem joined, particularly adapted for a human femur.

FIG. 2 is a bottom, perspective view of the head such as is depicted within FIG. 1.

FIG. 3 is a sectional view of the head of FIG. 1, taken in a plane which intersects the cylindrical axis thereof.

FIG. 4 is an enlarged, sectional view of part of the head of FIG. 1, taken generally within circle 4 of FIG. 3.

FIG. 5 is a sectional view of the head of FIG. 1, taken in the plane of FIGS. 4 resurfacing 5, with a standard taper gage inserted in its stem head receiving cup.

FIG. 6 is a side view of a short stemmed stem hereof.

FIG. 7 is a side view of a long stemmed stem such as is depicted within FIG. 1.

FIG. 8 is a side, sectional view of a modular ceramic ball and socket joint of the invention, including the components which are depicted in FIGS. 1–5 & 7, as implanted in a human hip joint.

DETAILED DESCRIPTION OF ILLUSTRATIVE EMBODIMENTS OF THE INVENTION

The invention can be further understood by the present detail which may be read in view of the drawings. The same should be taken in an illustrative and not necessarily limiting sense.

In general, the enarthrodial (ball and socket) type joint of the present invention includes a cupped ball head, preferably of ceramic and monolithic. The head is modular and is mounted with a stem. The modular cupped ball head and system subcombination is mated with the natural socket, or with an artificial head-receiving cup with the head-receiving articular cup mounted in suitable bone stock. Although the enarthrodial type joint implant may be for the shoulder, preferably the joint of concern is of the hip, and although the cupped ball head is preferably made of a suitable ceramic material to include of alumina and/or zirconia, the head and/or remaining components may be made of any suitable material.

With reference to FIGS. 1–8, modular ceramic ball and socket prosthetic hip joint 1000 includes ceramic and monolithic cupped ball head 100, for an example, of ZIRALLOY ceramic, as depicted in FIGS. 1–5 & 8; stem 200, preferably of metal, for example, a warm worked cobalt-chromium-molybdenum containing alloy, which is also termed Cobalt Chrome, such as described in the well-known ASTM-F799 or ASTM-1537, as depicted in FIGS. 1 & 6–8. Optionally implanted as part of the joint 1000 is head-receiving articular cup 300 such as having an all polyolefin construction, for example, of all ultra-high molecular weight polyethylene (UHMWPE) as depicted in FIG. 8, or a porous coated cobalt chrome backed polyethylene construction with back metal coxcomb type securing spikes, for example, as illustrated in the "BioPro Ceramic Tara" brochure. Alternatively, the cup 300 may be made of another suitable material or set of materials. The head 100 and stem 200 components may be assembled together, as shown in FIG. 1, with the subcombination suitably employed and assembled in conservative resurfacing joint replacement surgical procedures in conjunction with a natural articular surface receiving cup such as found with the natural glenoid or preferably the acetabular cavities; or, as may be indicated, directed or desired, all three components 100, 200 & 300 may be surgically mounted, for example, in suitable bone stock 7 as the conservative resurfacing replacement hip joint 1000, as depicted in FIG. 8. Beneficially however, as the situation may dictate, an acetabular cup such as the cup 300 may not be implanted, and the cupped ball head 100 of the modular joint 1000 is a femoral head implant which mates in articulative contact with the natural acetabulum of the hip.

With particular reference to FIGS. 2–5, the ceramic and monolithic cupped ball joint head 100 is structured about central axis 110 and includes support body 120. The support body 120 has inferior, deep, distally facing, generally if not quite precisely planar surface 122 with a substantially if not quite precisely circular outer boundary. Distally opening stem receiving bore 130 is centrally located in the support body 120, preferably concentric with the central axis 110 and containing smooth Morse taper side wall 132 and planar bore seat 134. Radius 136, for example, of a 0.020±0.020-inch size in standard head 100, may bridge the bore side wall 132 and seat 134. Chamfer 138, for example, of a 0.010±0.020-inch by 45-degree size in standard sized heads 100, may bridge the planar surface 122 and bore side wall 132. The head 100 also has cup wall 140 which extends distally from the support body 120. The cup wall 140 has a substantially if not quite precisely cylindrical inner surface 142 which generally extends from the outer boundary of the surface 122. Cup wall tip 144 defines an end of the cup wall 140. Chamfer 146, for example, of a 0.062±0.020-inch by 45-degree size in standard head 100, may bridge the surface 122 and cup wall inner surface 142. Thus, in general, a cup volume is defined by the features 122, 140, 142, 144, 146. The head 100 also includes superficially facing, generally if not quite precisely semispherical, low-friction, smooth external surface 150 which may be said to encapsulate the support body 120 and flange 140, and radius 152, for example, of a 0.020±0.020-inch size in standard sized heads 100, may bridge the flange tip 144 and polished head surface 150. The head 100 and its surface 150 may be manufactured to close tolerances, say, to a ±0.002-inch tolerance, or less, and it may be polished to a very close tolerance, for example to a ±2–3-millionths of an inch tolerance, or less, which is some four or five times more smooth than the polish on the known metal femoral hip replacement heads; owing to the smoothly polished ceramic head surface 150, the cupped ball head 100 generally not only has less wear than that of the known metal heads but also has increased smoothly articulating capability when mounted as part of a bone-preserving, conservative, resurfacing arthroplasty joint replacement. For example, in a standard 38-millimeter (38-mm) size, hip replacement head 100 can have a 1.494±0.002-inch spherical diameter 160 (twice the linear distance of the spherical radius), and the 0.002-inch tolerance can be retained in larger head 100 sizes. The surfaces 122, 132, 134, 136, 138, 142, 144, 146 & 152 typically are not polished.

In general, the ceramic head 100 is made by known methods, which may include grinding of ceramic starting material to a very fine powder; typically with an added stabilizer, heating, molding and cooling the powder to a solid ceramic in the desired shape; and polishing the articulating surface 150 as, for example, with a diamond sludge. In general, the ZIRALLOY ceramic head 100, which is of zirconium, partially stabilized with magnesium, is made in such a manner. After polishing, the ceramic head 100 in essence has an essentially perfect truncated spherical articulating surface 150.

Dimensions of the ceramic ball joint head may vary as needed for a particular application. For example, with the head 100 as a prosthetic part of the hip joint 1000, the following dimensions listed in inches, with ±0.010-inch tolerances unless otherwise noted, may be encountered in standard replacement joints sized as follows (FIGS. 3 & 5):

| No. | 38-mm | 41-mm | 43-mm | 45-mm | 47-mm | 49-mm | 51-mm | 53-mm | 55-mm |
| --- | --- | --- | --- | --- | --- | --- | --- | --- | --- |
| 160 | 1.494 +.002 | 1.612 +.002 | 1.691 +.002 | 1.770 +.002 | 1.848 +.002 | 1.927 +.002 | 2.006 +.002 | 2.086 +.002 | 2.165 +.002 |
| 161 | 1.363 ref. | 1.478 ref. | 1.549 ref. | 1.622 ref. | 1.693 ref. | 1.766 ref. | 1.839 ref. | 2.086 ref. | 2.165 ref. |
| 162 | 1.235 +.005 −.010 | 1.333 +.005 −.010 | 1.398 +.005 −.010 | 1.466 +.005 −.010 | 1.536 +.005 −.010 | 1.594 +.005 −.010 | 1.658 +.005 −.010 | 1.658 +.005 −.010 | 1.658 +.005 −.010 |
| 163 | 1.053 | 1.128 | 1.184 | 1.239 | 1.294 | 1.349 | 1.404 | 1.461 | 1.516 |
| 164 | 0.884 ref. | 0.963 ref. | 1.021 ref. | 1.078 ref. | 1.129 ref. | 1.169 ref. | 1.208 ref. | 1.208 ref. | 1.208 ref. |
| 165 | 0.484 | 0.563 | 0.621 | 0.678 | 0.729 | 0.769 | 0.808 | 0.808 | 0.808 |
| 166 | 2.192 +0.020 | 2.188 +0.020 | 2.186 +0.020 | 2.184 +0.020 | 2.188 +0.020 | 2.203 +0.020 | 2.219 +0.020 | 2.286 +0.020 | 2.331 +0.020 | and common to the foregoing particularly sized heads 100 are the following dimensions (FIGS. 4 & 5):

| No. | Value |
| --- | --- |
| 170 | 0.4602 - inch reference before radius 136. |
| 171 | 2-degree, 51-minute, 45-second ± 2-minute (2.8625-degree) half angle taper. |
| 172 | 0.4705 ± 0.0005 - inch dimension at dimension 173. |
| 173 | 0.113 ± 0.010 - inch dimension. |
| 174 | 0.4920 ± 0.0005 - inch dimension at dimension 175. |
| 175 | 0.328 ± 0.010 - inch dimension. |
| 177 | 0.400 + 0.000–0.005 - inch dimension. |
| 178 | 2.000 ± 0.010 - inch dimension. |
| 179 | 0.23 + 0.010–0.008 - inch dimension. |

With particular references to FIGS. 6 & 7, the stem 200, which is preferably made of a suitable metal or metal alloy, has distally directed spike 210 having upper shaft portion 212, which in general is radially symmetrical about the axis 110; blend 214; lower shaft portion 216; and rounded tip 218. The stem 200 has attached at the upper end of the spike 210 superior stem cap 220. The cap 220 preferably includes generally if not quite precisely radially symmetrical Morse taper side wall 222, generally if not precisely planar cylindrical top 224, and a bottom surface 225; thus, the cap 220 may be considered to be a trunion. Cap chamfer 226, may bridge the wall 222 and top 224, and lower cap radius 228 may bridge the underside of the cap 225 and the upper shaft portion 212. The cap 220 of the stem 220 is insertable into the stem cup 130 of the head 100. The stem 200 may be short (FIG. 6) or long (FIG. 7). The surfaces 220, 222, 224 & 226 may be polished.

In general, the stem 200 is made by known methods, which in the case of the metal stem 200 may include by casting or forging, or by any other suitable method known in the art. The stem 200 may be further machined or manipulated. For an example, the spike 210 may be bent, and grinding of the superior stem cap 220 may be carried out, as needed or desired. The whole stem 200 or part(s) thereof, optionally, may be polished. Bone-contacting parts of the stem 200 such as parts of the spike 210 may be metal-pore-coated such as by known methods. The Cobalt Chrome stem 200, in general, is made in such manner, with the spike 210 appropriately sized before bending. For an example, the long stem 200 (FIG. 7) may be turned to a 4.250±1.010-inch length before bending.

Dimensions of the stem may vary as needed for a particular application. For example, with the stem 200 as a prosthetic part of the hip joint 1000, with dimensions listed in inches, and with ±0.010-inch tolerances unless otherwise noted, may be encountered in standard replacement joints, as follows:

| No. | Short Stem | Long Stem |
|-----|------------|-----------|
| 230 | 2.8 ± 0.120 | 3.80 ± 0.120 |
| 231 | 2.699 | 3.699 |
| 232 | 1.20 ± 0.20 | 1.391 |
| 233 | 0.595 | 0.975 | and common to the foregoing particularly sized stems 200 are the following dimensions (FIGS. 6 & 7):

| No. | Value |
|-----|-------|
| 240 | 0.4986 ± 0.005 - inch dimension. |
| 241 | 0.4625 - inch reference before chamfer 226. |
| 242 | 0.425 ± 0.010 - inch dimension. |
| 243 | 2-degree, 47-minute, 45-second ± 1-minute (2.7958-degree) half angle taper. |
| 244 | 0.370 + 0.000–0.005 - inch dimension. |
| 245 | 0.300 ± 0.010 - inch diameter. |
| 246 | 3.00 ± 0.020 - inch dimension. |
| 247 | 3.30 ± 0.020 - inch radius. |
| 248 | 3.000 ± 0.010 - inch radius. |
| 249 | 64 ± 1 - degree angle. |
| 250 | 0.200 ± 0.010 - inch diameter. |

Thus, the Morse taper can be, for example, of a 12/14-size.

In the practice of the invention, for bone-preserving, conservative, femoral resurfacing arthroplasty hip replacement surgery where an acetabular cup replaces the acetabulum, the femoral head 100 and acetabular cup 300 components for resurfacing can be made available in matching sizes, for example, size sizes, ranging from a 38-mm to a 49-mm size. The femoral head component 100 can also be made available in those sizes and in three additional larger sizes from a 51-mm to 55 -mm size in the interest of providing a complete complement of components for use, in particular, for hemiarthroplasty with a natural acetabulum. Thus, a sufficient range of sizes of the components 100 & 300 are made available to not only accommodate their use for total articular replacement but also to assure a reasonably precise acetabular fit for the hemiarthroplasty resurfacing operation without the cup 300. The interchangeable, modular, femoral stems 200 with Morse fitting trunion for the femoral head component 100 can be made in at least two lengths, standard, i.e., long, and short. The short femoral stem 200 (FIG. 6) is indicated in the face of an obstruction in the proximal medullary canal owing to an old fracture or a prior corrective osteotomy, or in the presence of a significant varus deformity. In the surgical attachment of the femoral component 100/200 and/or the acetabular component 300 of the joint 1000 to the pertinent bone stock, a layer of surgical cement 101 and/or 301, for example, a surgical cement of a polymethylmethacrylate polymer curable in vivo, can be generally employed. See, e.g., Townley, *Orthopedic Clinics of North America,* Vol. 13, No. 4, October 1982; BioPro, Inc., "The Biopro Tara Surgical Procedure" brochure. See also, the brochure from BioProd, Inc., circa March, 1998, "Total Articular Replacement Arthroplasty for the Hip Joint, T.A.R.A., Utilizing Ceramic-on-Polyethylene."

In general, although certain specific materials, shapes and units of measure have been set forth herein, the invention may be subject to appropriate variability.

Accordingly, the first component of the invention, the cupped ball head 100, can be made of any suitable material, to include a suitable metal or metal alloy, and it can be designed with any suitable configuration. For example, the configuration of the inner cup to volume 122, 140, 142 et seq., for mating with resected femoral bone stock, may be of any suitable sort, to include having scored or grooved surfaces, variable degrees of marginal chamfering; having a polygonal, for example, a squared, or a curvilinear, for example, a spherical, elliptical, cylindrical, form; or any form geometrically configured otherwise, or having any suitable depth. A preferred embodiment of the invention, with the head monolithic 100 made of the ceramic, has the configuration of the inner cup volume 122, 140, 142 et seq., in a cylindrically configured form with vertically parallel side walls 142 and a flat, slightly chamfered top surface 122. The articulating outer dimension of the cupped ball component 100 varies incrementally in diameter to accommodate the anatomical variability in the size of the femoral head in a given patient. In various embodiments in the practice of the present invention, the diameter of the cupped ball head 100 can vary in size from the 38-mm to 55-mm sizes; however, the invention does not necessarily exclude other greater or lesser diameters to the head 100, nor does it necessarily exclude greater or lesser increments between sizes.

As well, the second component of the invention, the stem 200, can be made of any suitable material, which may include a suitable engineering plastic and/or ceramic but preferably is of metal or metal alloy, and it can be configured with any suitable shape or form. For example, forms may include numerous straight and variably curved configurations; variable placement of any curvature to its spike 210; any suitable length or diameter for the spike 210; and any suitable cross-sectional configuration to the spike 210 or cap 220, which may include radially, rotationally infinitely symmetrical, polygonal to include triangulated, squared and so forth, curvilinear to include elliptical, or any other suitable geometrically configured form. A preferred embodiment of the configuration of the stem 200 of the present invention is made to conform to the intramedullary anatomy of the proximal femur and is fabricated in two lengths to accommodate variable anatomical or pathologically induced anomalies in the configuration of the medullary canal. The upper cap 220 for conjoining with the bore 130 of the head 100 is preferably made with a radially, rotationally infinitely symmetrical, or "round," slightly angled wall configuration which conforms to the inner dimension of the receptacle 130 in the head 100 in a manner which will provide a stable Morse fit between the two modular parts of the assembled composite prosthesis.

In the preferred embodiments of the invention, particularly as concerns the ceramic head, dimensions of the ceramic may be different from those which would otherwise be found with respect to the corresponding metal component, and as a consequence, the metal stem may be made to be more compact. However that may be, in addition to the fact that the ceramic is more desirable from the standpoint of friction considerations, it is generally more biocompatible.

Hip joints 1000 of the invention, having the ZIRALLOY ceramic cupped ball heads 100 and Cobalt Chrome stems 200, have been implanted in a number of patients, including conservative total articular resurfacings and conservative hemiarthroplasty resurfacings. Results of surgeries with the joints 1000 have been determined to be successful.

Analogous component assemblies may be made available for employment with other enarthrodial joints such as, for example, the shoulder. Of course, the actual materials employed and sizes manufactured and used are desirably determined by the joint under consideration.

CONCLUSION

The present invention is thus provided. Various parts and subcombinations may be practiced without reference to other parts and subcombinations, and numerous modifications can be effected within the spirit of the invention, the literal claim scope of which is particularly pointed out as follows:

I claim:

1. A modular, bone-preserving, conservative resurfacing arthroplasty ball and socket joint implant, comprising the following components:

a ceramic and monolithic cupped ball head, said head having a generally semispherical, smooth external bearing surface and an inner support body with an inferior, deep, distally facing surface having an outer boundary thereto, said support body having a distally opening stem receiving bore centrally located therein; a part of said bearing surface and an inner surface defining a cup wall, extending distally from said support body from said outer boundary of said distally facing surface; and a stem, which is an elongated member having a distally directed spike, and a proximal stem cap, which is insertable into said bore of said head;

wherein:

said stem cap, is insertably and frictionally attached to said stem bore.

2. The joint implant of claim 1, wherein the external bearing surface of said head has a low friction coefficient; said bore and stem cap have a tapered connection; and the joint implant is a hip joint implant.

3. The joint implant of claim 2, wherein said head has a minimum diameter of about 38 mm.

4. The joint implant of claim 3, wherein said bore and said stem cap are provided with Morse tapers.

5. The joint implant of claim 4, wherein said distally facing surface of the support body is planar, terminating in a chamfered outer edge; said bore is centrally located in the support body; and said cup wall has a cylindrical surface.

6. The joint implant of claim 1, further comprising a head-receiving articular cup.

7. The joint implant of claim 2, further comprising a head-receiving acetabular cup.

8. A ceramic cupped ball joint head component for a modular, bone-preserving, conservative, resurfacing arthroplasty, ball and socket joint implant, said head component comprising a generally semispherical, low friction, smooth external bearing surface and an inner support body with an inferior, deep, distally facing surface having a substantially circular outer boundary thereto; a distally opening stem receiving bore centrally located in the support body; a part of said bearing surface and an inner surface defining a cup wall, extending distally from said support body from said outer boundary of said surface.

9. The head of claim 8, wherein said distally facing surface of said support body is generally planar; said cup wall is substantially cylindrical; the stem receiving bore is radially symmetrical and has a Morse taper, and the ball and socket joint is a hip joint.

10. A stem for a modular, bone-preserving conservative, resurfacing arthroplasty, ball and socket joint implant, said stem comprising a distally directed, elongated spike insertable into suitable bone stock; and a superiorly connected stem cap, tapering inwardly in a superior direction, which is insertable into a stem bore of a corresponding cupped ball joint head for said modular joint implant.

11. The stem of claim 10, which is a femoral component wherein the spike is configured for intramedullary insertion through a resected neck of a human femur, and the ball and socket joint implant is a hip joint.

12. The stem of claim 11, wherein the spike is curved.

13. The stem of claim 11, wherein the spike is straight.

14. The stem of claim 10, wherein the stem is made of metal or metal alloy.

15. The stem of claim 11, wherein the stem is made of metal or metal alloy.

16. The stem of claim 12, wherein the stem is made of metal or metal alloy.

17. The stem of claim 13, wherein the stem is made of metal or metal alloy.

18. The stem of claim 15, wherein said superior stem cap defines a Morse taper.

* * * * *

UNITED STATES PATENT AND TRADEMARK OFFICE
CERTIFICATE OF CORRECTION

PATENT NO. : 6,096,084
DATED : August 1, 2000
INVENTOR(S): Charles O. Townley

It is certified that error appears in the above-identified patent and that said Letters Patent is hereby corrected as shown below:

At col. 1, line 35, delete "not" and insert therefor -- now --.

At col. 1, line 37, capitalize the initial letter "c."

At col. 3, lines 4-5, between "body;" and "a cup wall" there is no paragraph separation.

At col. 3, line 60, delete "resurfacing" and insert therefor -- & --.

At col. 6, line 5, delete all nine occurrences of "+.002" and insert for each -- $\pm.002$ --.

At col. 6, line 19, delete all nine occurrences of "+0.020" and insert for each -- $\pm 0.020$ --.

At col. 6, line 64, delete "4.250±1.010 - inch" and insert therefor -- 4.250±0.010 - inch --.

At col. 7, line 37, delete "size" and insert therefor -- six --.

UNITED STATES PATENT AND TRADEMARK OFFICE
CERTIFICATE OF CORRECTION

PATENT NO. : 6,096,084
DATED : August 1, 2000
INVENTOR(S) : Charles O. Townley

It is certified that error appears in the above-identified patent and that said Letters Patent is hereby corrected as shown below:

At col. 7, line 61, delete "Bioprod," and insert therefor
-- BioPro, --.

At col. 10, line 13, i.e., claim 8, line 10, delete "said" and insert therefor -- the --.

Signed and Sealed this

Seventeenth Day of April, 2001

Attest:

NICHOLAS P. GODICI

Attesting Officer     Acting Director of the United States Patent and Trademark Office